(12) United States Patent
Tamai et al.

(10) Patent No.: US 6,790,865 B2
(45) Date of Patent: Sep. 14, 2004

(54) 2-METHYLPROPIONIC ACID DERIVATIVES AND PHARMACEUTICAL COMPOSITIONS COMPRISING THE SAME

(75) Inventors: Tetsuro Tamai, Nagano (JP);
Nobuyuki Tanaka, Nagano (JP);
Harunobu Mukaiyama, Nagano (JP);
Akihito Hirabayashi, Nagano (JP);
Hideyuki Muranaka, Nagano (JP);
Masaaki Sato, Nagano (JP); Masuo Akahane, Nagano (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 0 days.

(21) Appl. No.: 10/358,214

(22) Filed: Feb. 5, 2003

(65) Prior Publication Data

US 2003/0166719 A1 Sep. 4, 2003

Related U.S. Application Data

(63) Continuation of application No. 09/673,308, filed as application No. PCT/JP99/01836 on Apr. 7, 1999.

(30) Foreign Application Priority Data

Apr. 14, 1998 (JP) ............................................ 10-142028

(51) Int. Cl.[7] ..................... A61K 31/24; A61K 31/195; C07C 229/00
(52) U.S. Cl. .................. 514/539; 514/567; 560/39; 562/444
(58) Field of Search ................................ 514/539, 567; 560/39; 562/444

(56) References Cited

U.S. PATENT DOCUMENTS

| 4,146,638 A | 3/1979 | Renth et al. |
| 4,338,333 A | 7/1982 | Ainsworth et al. |
| 6,353,025 B1 | 3/2002 | Tamai et al. |
| 6,399,660 B1 | 6/2002 | Tamai et al. |

FOREIGN PATENT DOCUMENTS

| JP | WO98/1333 | 2/1998 |
| JP | WO99/05090 | 4/1999 |

OTHER PUBLICATIONS

International Search Report Jun. 1999.

*Primary Examiner*—Johann Richter
*Assistant Examiner*—Paul A. Zucker
(74) *Attorney, Agent, or Firm*—Sughrue Mion, PLLC

(57) ABSTRACT

The present invention provides novel 2-methylpropionic acid derivatives represented by the general formula:

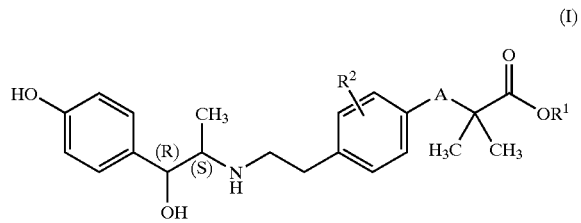

(I)

(wherein $R^1$ represents a hydrogen atom, a lower alkyl group or an aralkyl group; $R^2$ represents a hydrogen atom, a lower alkyl group or a halogen atom; A represents an oxygen atom or an imino group; the carbon atom marked with (R) represents a carbon atom in R configuration; and the carbon atom marked with (S) represents a carbon atom in S configuration) and pharmaceutically acceptable salts thereof, which have excellent $\beta_3$-adrenoceptor stimulating effects and are useful as agents for the prevention or treatment of obesity, hyperglycemia, the diseases caused by intestinal hypermotility, pollakiuria, urinary incontinence, depression, or the diseases caused by biliary calculi or hypermotility of the biliary tract.

10 Claims, No Drawings

2-METHYLPROPIONIC ACID DERIVATIVES AND PHARMACEUTICAL COMPOSITIONS COMPRISING THE SAME

This is a continuation of Application No. 09/673,308 filed Oct. 13, 2000; the disclosure of which is incorporated herein by reference. Application No. 09/673,308 is the US National State Entry under 35 U.S.C. § 371 of PCT/JP99/01836 filed Apr. 7, 1999.

TECHNICAL FIELD

The present invention relates to novel 2-methylpropionic acid derivatives and pharmaceutically acceptable salts thereof which are useful as medicaments.

BACKGROUND ART

It is known that three subtypes of sympathetic β-adrenoceptors, which have been classified as $β_1$, $β_2$ and $β_3$, are present and that each receptor subtype is distributed in specified organs in living body and has a specific function.

For example, $β_1$-adrenoceptor is mainly present in the heart and the stimulation of this receptor leads to an increase of heart rate and cardiac contractility. $β_2$-Adrenoceptor is mainly present in the smooth muscle of blood vessels, the trachea and uterus. The stimulation of this receptor leads to vasodilatation, bronchodilation and inhibition of uterine contraction. $β_3$-Adrenoceptor is mainly present in adipocytes, the gallbladder and intestinal tract. It is known that $β_3$-adrenoceptor is also present in the brain, liver, stomach and prostate. It is reported that the stimulation of this receptor leads to an increase of lipolysis, inhibition of intestinal tract motility, an increase of glucose uptake, anti-depression and so on (Drugs of the Future, Vol.18, No.6, pp.529–549 (1993); Molecular Brain Research, Vol.29, pp.288–297 (1995);

In addition, it is recently reported that in the human bladder $β_3$-adrenoceptor is predominantly present and that the human bladder is relaxed by $β_3$-adrenoceptor stimulants (The Japanese Journal of Urology, Vol.88, No.2, p.183 (1997); NEUROUROLOGY AND URODYNAMICS, Vol.16, No.5, pp.363–365 (1997)).

Many $β_1$-adrenoceptor stimulants and $β_2$-adrenoceptor stimulants have been developed and are used for medicinal purposes as cardiotonics, bronchodilators, preventive agents for threatened abortion or premature labor, and so on.

On the other hand, it has been found that $β_3$-adrenoceptor stimulants are useful as agents for the prevention or treatment of obesity, hyperglycemia, the diseases caused by intestinal hypermotility, pollakiuria, urinary incontinence, depression, the diseases caused by biliary calculi or hypermotility of biliary tract and so on. Consequently, studies have been made to develop excellent $β_3$-adrenoceptor stimulants, but no $β_3$-adrenoceptor stimulant has been sold yet (Drugs of the Future, Vol.18, No.6, pp.529–549(1993); European Journal of Pharmacology, Vol.219, pp.193–201 (1992) etc.).

Therefore, it has been greatly desired to develop novel $β_3$-adrenoceptor stimulants having excellent $β_3$-adrenoceptor stimulating effects.

More preferably, it has been desired to develop highly selective and novel $β_3$-adrenoceptor stimulants having potent $β_3$-adrenoceptor stimulating effects in comparison with $β_1$ and/or $β_2$-adrenoceptor stimulating effects and resulting in reduced side effects such as palpitation and tremor caused by $β_1$ and β2-adrenoceptor stimulating effects.

DISCLOSURE OF THE INVENTION

The present invention relates to a 2-methylpropionic acid derivative represented by the general formula:

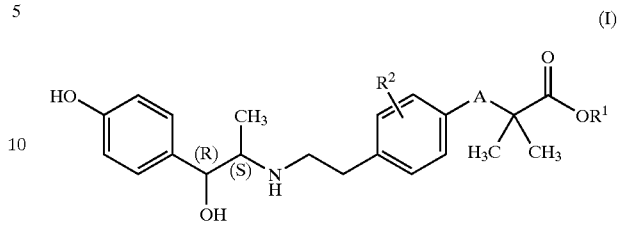

(I)

(wherein $R^1$ represents a hydrogen atom, a lower alkyl group or an aralkyl group; $R^2$ represents a hydrogen atom, a lower alkyl group or a halogen atom; A represents an oxygen atom or an imino group; the carbon atom marked with (R) represents a carbon atom in R configuration; and the carbon atom marked with (S) represents a carbon atom in S configuration) or a pharmaceutically acceptable salt thereof.

The present invention relates to a pharmaceutical composition comprising as the active ingredient a 2-methylpropionic acid derivative represented by the above general formula (I) or a pharmaceutically acceptable salt thereof.

The present invention relates to an agent for the prevention or treatment of obesity, hyperglycemia, the diseases caused by intestinal hypermotility, pollakiuria, urinary incontinence, depression, or the diseases caused by biliary calculi or hypermotility of biliary tract which comprises as the active ingredient a 2-methylpropionic acid derivative represented by the above general formula (I) or a pharmaceutically acceptable salt thereof.

The present invention relates to a method for the prevention or treatment of obesity, hyperglycemia, the diseases caused by intestinal hypermotility, pollakiuria, urinary incontinence, depression, or the diseases caused by biliary calculi or hypermotility of biliary tract which comprises administering a therapeutically effective amount of a 2-methylpropionic acid derivative represented by the above general formula (I) or a pharmaceutically acceptable salt thereof.

The present invention relates to a use of a 2-methylpropionic acid derivative represented by the above general formula (I) or a pharmaceutically acceptable salt thereof for the manufacture of a pharmaceutical composition for the prevention or treatment of obesity, hyperglycemia, the diseases caused by intestinal hypermotility, pollakiuria, urinary incontinence, depression, or the diseases caused by biliary calculi or hypermotility of biliary tract.

The present invention relates to a use of a 2-methylpropionic acid derivative represented by the above general formula (I) or a pharmaceutically acceptable salt thereof as an agent for the prevention or treatment of obesity, hyperglycemia, the diseases caused by intestinal hypermotility, pollakiuria, urinary incontinence, depression, or the diseases caused by biliary calculi or hypermotility of biliary tract.

The present invention relates to a process for the manufacture of a pharmaceutical composition for the prevention or treatment of obesity, hyperglycemia, the diseases caused by intestinal hypermotility, pollakiuria, urinary incontinence, depression, or the diseases caused by biliary calculi or hypermotility of biliary tract, characterized in the use, as an essential constituent, of a 2-methylpropionic acid derivative represented by the above general formula (I) or a pharmaceutically acceptable salt thereof.

BEST MODE FOR CARRYING OUT THE INVENTION

The present inventors have studied extensively to meet the above objects. As a result, it was found that 2-methylpropionic acid derivatives represented by the above general formula (I) and pharmaceutically acceptable salts thereof have excellent $\beta_{2,3}$-adrenoceptor stimulating effects, thereby forming the basis of the present invention.

In the present invention, the term "lower alkyl group" means a straight or branched alkyl group having 1 to 6 carbon atoms such as a methyl group, an ethyl group, a propyl group, an isopropyl group, a butyl group, a sec-butyl group, a tert-butyl group, an isobutyl group, a pentyl group, an isopentyl group, a hexyl group and the like; the term "aralkyl group" means the above lower alkyl group substituted by an aryl group such as a phenyl group, a naphthyl group and the like; and the term "halogen atom" means a fluorine atom, a chlorine atom, a bromine atom and the like.

The compounds represented by the above general formula (I) of the present invention can be prepared according to the following procedure. For example, the compounds of the present invention can be prepared by allowing an amine compound represented by the formula:

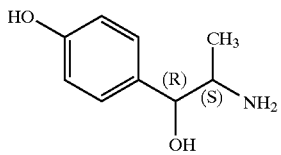

(II)

(wherein the carbon atom marked with (R) and the carbon atom marked with (S) have the same meanings as defined above) to react with an alkylating agent represented by the general formula:

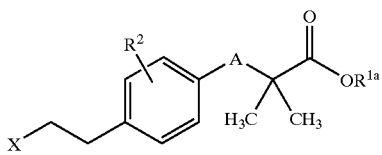

(III)

(wherein $R^{1a}$ represents a lower alkyl group or an aralkyl group; X represents a leaving group; and $R^2$ and A have the same meanings as defined above) in the presence or absence of a base such as N,N-diisopropylethylamine in an inert solvent such as N,N-dimethylformamide, and converting the ester group into a carboxyl group in the usual way as occasion demands.

The amine compound represented by the above formula (II) which is used as a starting material in the above production process can be prepared by optical resolution of a commercially available enantiomeric mixture in the usual way or a method described in a literature (e.g., J. Med. Chem., Vol. 20, No. 7, pp.978–981(1977)).

The compounds represented by the above general formula (III) which are used as starting materials in the above production process can be prepared according to the following procedures. For example, the compounds can be prepared by allowing a compound represented by the general formula:

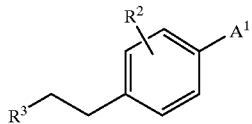

(IV)

(wherein $R^3$ represents a hydroxy group having a protective group; $A^1$ represents a hydroxy group or an amino group; and $R^2$ has the same meaning as defined above) to react with 1,1,1-trichloro-2-methyl-2-propanol or chloroform in the presence of a base such as potassium hydroxide or sodium hydroxide in acetone, subjecting the resulting compound to esterification in the usual way to give a compound represented by the general formula:

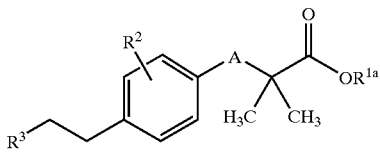

(V)

(wherein $R^{1a}$, $R^2$, $R^3$ and A have the same meanings as defined above), removing the hydroxy-protective group and converting the hydroxy group into a leaving group in the usual way.

Of the compounds represented by the above general formula (III) which are used in the above production process, the compounds represented by the general formula:

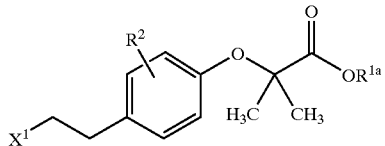

(IIIa)

(wherein $X^1$ represents a chlorine atom or a bromine atom; and $R^{1a}$ and $R^2$ have the same meanings as defined above) can be prepared by subjecting a compound represented by the general formula:

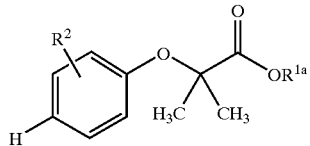

(VI)

(wherein $R^{1a}$ and $R^2$ have the same meanings as defined above) to Friedel-Crafts reaction using an acid halide represented by the general formula:

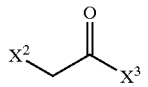

(VII)

(wherein $X^2$ represents a hydrogen atom, a chlorine atom or a bromine atom; and $X^3$ represents a chlorine atom or a bromine atom), subjecting the resulting compound to bromination or chlorination of the acetyl group in the usual way as occasion demands, and reducing the carbonyl group at the benzyl position using a reducing agent such as triethylsilane.

The compounds represented by the above general formula (VI) which are used as starting materials in the above production process can be prepared, for example, 1) by allowing a compound represented by the general formula:

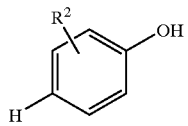

(VIII)

(wherein $R^2$ has the same meaning as defined above) to react with 1,1,1-trichloro-2-methyl-2-propanol or chloroform in the presence of a base such as potassium hydroxide or sodium hydroxide in acetone and subjecting the resulting compound to esterification in the usual way, or 2) by allowing a compound represented by the above general formula (VIII) to react with an alkyl 2-bromoisobutyrate in the presence of a base such as cesium carbonate in N,N-dimethylformamide.

The compounds represented by the above general formula (IV) which are used as starting materials in the above production process can be prepared by using the corresponding phenol derivative or aniline derivative according to methods described in the literature or methods analogous thereto (Org. Synth., collect. Vol.111, pp.183–184(1955); J. Med. Chem., Vol.15, No.5, pp.490–493(1972); J. Med. Chem., Vol.28, No.12, pp.1828–1832(1985) etc.).

For example, the compounds represented by the above general formula (IV) can be prepared by subjecting a compound represented by the general formula:

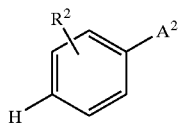

(IX)

(wherein $A^2$ represents a protected hydroxy group or a protected amino group; and $R^2$ has the same meaning as defined above) to Friedel-Crafts reaction using bromoacetyl bromide to give a compound represented by the general formula:

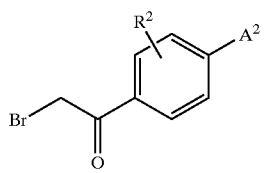

(X)

(wherein $R^2$ and $A^2$ have the same meanings as defined above), reducing the compound with a reducing agent such as sodium borohydride, treating the resulting compound with a base such as potassium carbonate to give an epoxy compound represented by the general formula:

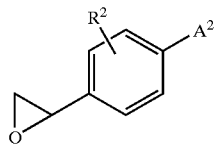

(XI)

(wherein $R^2$ and $A^2$ have the same meanings as defined above), opening the epoxy group in the usual way, subjecting the resulting compound to protection of the resulting alcoholic hydroxy group and removing the protective group of the phenolic hydroxy group or the amino group in the usual way.

The compounds represented by the above general formula (IV) can be prepared by subjecting the phenolic hydroxy group or the amino group of a compound represented by the general formula:

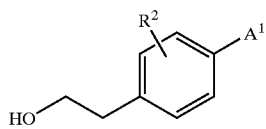

(XII)

(wherein $R^2$ and $A^1$ have the same meanings as defined above) to protection temporarily using chloromethyl methyl ether, trifluoroacetic anhydride or the like, converting the alcoholic hydroxy group of the resulting compound into a hydroxy-protective group which is stable under an alkaline condition such as a benzyl ether, a benzyloxymethyl ether or the like, and removing the protective group of the phenolic hydroxy group or the amino group in the usual way.

Of the compounds represented by the above general formula (IV), the compounds represented by the general formula:

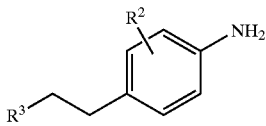

(IVa)

(wherein $R^2$ and $R^3$ have the same meanings as defined above) can be prepared by converting the alcoholic hydroxy group of a compound represented by the general formula:

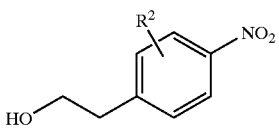

(XIII)

(wherein $R^2$ has the same meaning as defined above) into a protective group which is stable under an alkaline condition such as a benzyl ether, a benzyloxymethyl ether, methoxymethyl ether or the like, and reducing the nitro group in the usual way.

In the above production process, the term "leaving group" means a leaving group generally used for N-alkylation such as a p-toluenesulfonyloxy group, a methanesulfonyloxy group, a chlorine atom, a bromine atom, an iodine atom and the like.

The 2-methylpropionic acid derivatives represented by the above general formula (I) of the present invention can be converted into their pharmaceutically acceptable salts in the usual way. Examples of such salts include acid addition salts formed with mineral acids such as hydrochloric acid, hydrobromic acid, hydroiodic acid, sulfuric acid, nitric acid, phosphoric acid and the like; acid addition salts formed with organic acids such as formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid and the like; inorganic base salts such as a sodium salt, a potassium salt, a calcium salt and the like; and salts formed with organic bases such as triethylamine, piperidine, morpholine, pyridine, lysine and the like.

The compounds of the present invention obtained by the above production process can be isolated and purified by conventional separation means such as fractional recrystallization, purification using chromatography and solvent extraction.

The compounds of the present invention include their solvates with pharmaceutically acceptable solvents such as water and ethanol.

$\beta_3$-Adrenoceptor stimulating effects of the compounds represented by the above general formula (I) of the present invention were studied according to the following procedure.

Namely, urinary bladders of ferrets were isolated and preparations were made. The experiment was conducted according to the Magnus method. The ureteral tension without the addition of the drug is expressed as 100%, and the tension of maximal relaxation after the addition of $10^{-5}$M of forscolin was expressed as 0%. The drug was added cumulatively. The $\beta_3$-adrenoceptor stimulating effects were evaluated as the concentration of the drug required to produce 50% decrease of the tension (i.e., $EC_{50}$ value) (The Japanese Journal of Urology, Vol.89, No.2, p.272 (1998)).

For example, $\beta_3$-adrenoceptor stimulating effect ($EC_{50}$ value) of 2-[3-chloro-4-[2-[[(1S,2R)-2-hydroxy-2-(4-hydroxyphenyl)-1-methylethyl]amino]ethyl]phenoxy]-2-methylpropionic acid was $1.9 \times 10^{-8}$M.

Thus, the compounds represented by the above general formula (I) of the present invention are excellent $\beta_3$-adrenoceptor stimulants having excellent $\beta_3$-adrenoceptor stimulating effects.

As preferable compounds in the present invention, 2-methyipropionic acid derivatives represented by the general formula:

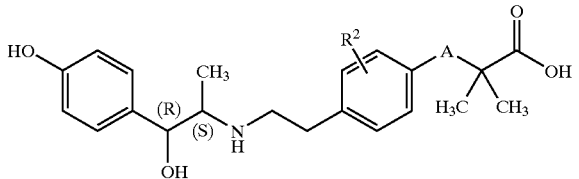

(Ia)

(wherein $R^2$, A, the carbon atom marked with (R) and the carbon atom marked with (S) have the same meanings as defined above) and pharmaceutically acceptable salts thereof having potent $\beta_3$-adrenoceptor stimulating effects compared with $\beta_1$ and $\beta_2$-adrenoceptor stimulating effects can be illustrated.

The $\beta_1$-adrenoceptor stimulating effects and $\beta_2$-adrenoceptor stimulating effects of the compounds represented by the above general formula (I) of the present invention were studied according to the following procedures.

Namely, atria of rats were isolated and preparations were made. The experiment was conducted according to the Magnus method. The increment of heart rate after the addition of isoproterenol ($10^{-8}$M) was expressed as 100%. The drug was added cumulatively. The $\beta_1$-adrenoceptor stimulating effects were evaluated as the concentration of the drug required to produce 50% increase of heart rate (i.e., $EC_{50}$ value).

Also, uteri of pregnant rats were isolated and preparations were made. The experiment was conducted according to the Magnus method. The sum of uterine contractions during 5 minutes before the addition of the drug was expressed as 100%. The drug was added cumulatively. The $\beta_2$-adrenoceptor stimulating effects were evaluated as the concentration of the drug required when the sum of the contractions during 5 minutes after the addition of the drug produces 50% decrease of the sum of the contractions during 5 minutes before the addition of the drug (i.e., $EC_{50}$ value).

For example, $\beta_1$ and $\beta_2$-adrenoceptor stimulating effects of 2-[3-chloro-4-[2-[[(1S,2R)-2-hydroxy-2-(4-hydroxyphenyl)-1-methylethyl]amino]ethyl]phenoxy]-2-methylpropionic acid were $3.5 \times 10^{-5}$M ($EC_{50}$ value) and $3.1 \times 10^{-6}$M ($EC_{50}$ value), respectively. This compound is an extremely suitable compound as an excellent $\beta_3$-adrenoceptor stimulant with highly reduced $\beta_1$ and $\beta_2$-adrenoceptor stimulating effects.

The 2-methyipropionic acid derivatives represented by the above general formula (I) and pharmaceutically acceptable salts thereof of the present invention have excellent $\beta_3$-adrenoceptor stimulating effects and are very useful compounds as medicaments such as an agent for the prevention or treatment of obesity, hyperglycemia, the diseases caused by intestinal hypermotility, pollakiuria, urinary incontinence, depression, the diseases caused by biliary calculi or hypermotility of biliary tract, or the like.

Furthermore, the compounds represented by the above general formula (I) of the present invention are very safe compounds. For example, in acute toxicity testing using rats, when 2-[3-chloro-4-[2-[[(1S,2R)-2-hydroxy-2-(4-hydroxyphenyl)-1-methylethyl]amino]ethyl]phenoxy]-2-methylpropionic acid was administered at a dose of 400 mg/kg, no death was observed.

When the 2-methylpropionic acid derivatives represented by the above general formula (I) and pharmaceutically acceptable salts thereof of the present invention are employed in the practical treatment, they are administered orally or parenterally in the form of compositions such as powders, granules, fine granules, tablets, capsules, injections, solutions, ointments, suppositories and the like. These pharmaceutical compositions can be formulated in accordance with conventional methods using conventional pharmaceutical carriers, excipients and other additives.

The dosage is appropriately decided depending on the type of diseases, age, sex, body weight, degree of symptoms and the like of each patient to be treated, which is approximately within the range of from 1 to 1,000 mg per day per adult human in the case of oral administration and approximately within the range of from 0.01 to 100 mg per day per adult human in the case of parenteral administration, and the daily dose can be divided into one to several doses per day.

The present invention is further illustrated in more detail by way of the following Reference Examples, Examples and Test Examples. However, the present invention is not limited thereto.

REFERENCE EXAMPLE 1

Ethyl 2-[4-(2-bromoacetyl)-3-chlorophenoxy]-2-methylpropionate

To a solution of 3-chlorophenol (5.0 g) in acetone (100 ml) were added potassium hydroxide (19.5 g) and 1,1,1-trichloro-2-methyl-2-propanol hydrate (13.7 g), and the mixture was stirred for 14 hours at room temperature. After the reaction mixture was concentrated under reduced pressure, water was added to the residue, and the mixture was washed with ethyl acetate. The aqueous layer was acidified with concentrated hydrochloric acid and extracted with ethyl acetate. The extract was washed with water and brine, and dried over anhydrous magnesium sulfate, and the solvent was removed under reduced pressure. The residue was dissolved in ethanol (150 ml) a catalytic amount of sulfuric acid was added to the solution, and the mixture was heated under reflux for 22 hours. After the reaction mixture was concentrated under reduced pressure, the residue was dissolved in ethyl acetate, washed with water, a saturated aqueous sodium bicarbonate solution and brine subsequently, and dried over anhydrous magnesium sulfate. Removal of the solvent under reduced pressure gave ethyl 2-(3-chlorophenoxy)-2-methylpropionate (5.8 g).

To a stirred suspension of aluminum chloride (1.8 g) in 1,2-dichloroethane (25 ml) was added bromoacetyl bromide (400 μl) under ice-cooling, and the mixture was stirred for 30 minutes. To the stirred mixture was added dropwise a solution of ethyl 2-(3-chlorophenoxy)-2-methylpropionate (1.1 g) in 1,2-dichloroethane (5 ml) under ice-cooling, and the mixture was stirred for 3 hours at 60° C. The reaction mixture was poured into ice-water and extracted with ethyl acetate. The extract was washed with water and dried over anhydrous magnesium sulfate, and the solvent was removed under reduced pressure. Purification of the residue by flash column chromatography on silica gel (eluent: hexane/ethyl acetate=10/1) gave ethyl 2-[4-(2-bromoacetyl)-3-chlorophenoxy]-2-methylpropionate (204 mg).

$^1$H-NMR(CDCl$_3$) δ ppm: 1.24 (3H, t, J=7.1 Hz), 1.65 (6H, s), 4.24 (2H, q, J=7.1 Hz), 4.53 (2H, s), 6.74 (1H, dd, J=8.7, 2.5 Hz), 6.89 (1H, d, J=2.5 Hz), 7.62 (1H, d, J=8.7 Hz)

REFERENCE EXAMPLE 2

The following compounds were prepared according to a similar manner to that described in Reference Example 1 using the corresponding phenol derivative.

Ethyl 2-[4-(2-bromoacetyl)-2-chlorophenoxy]-2-methylpropionate $^1$H-NMR(CDCl$_3$) δ ppm: 1.24 (3H, t, J=7.1 Hz), 1.70 (6H, s), 4.24 (2H, q, J=7.1 Hz), 4.36 (2H, s), 6.81 (1H, d, J=8.7 Hz), 7.78 (1H, dd, J=8.7, 2.3 Hz), 8.04 (1H, d, J=2.3 Hz)

Ethyl 2-[4-(2-bromoacetyl)-2-methylphenoxy]-2-methylpropionate $^1$H-NMR(CDCl$_3$) δ ppm: 1.26 (3H, t, J=7.1 Hz), 1.67 (6H, s), 2.28 (3H, s), 4.23 (2H, q, J=7.1 Hz), 4.39 (2H, s), 6.62 (1H, d, J=8.6 Hz), 7.72 (1H, dd, J=8.6, 2.3 Hz,), 7.81 (1H, d, J=2.3 Hz)

REFERENCE EXAMPLE 3

Ethyl 2-[4-(2-bromoethyl)-3-chlorophenoxy]-2-methylpropionate

To a solution of ethyl 2-[4-(2-bromoacetyl)-3-chlorophenoxy]-2-methylpropionate (209 mg) in trifluoroacetic acid (445 μl ) was added triethylsilane (300 μl), and the mixture was stirred for 1 hour at 60° C. After the reaction mixture was concentrated under reduced pressure, purification of the residue by medium pressure liquid column chromatography on silica gel (eluent: hexane/ethyl acetate=30/1) gave ethyl 2-[4-(2-bromoethyl)-3-chlorophenoxy]-2-methylpropionate (171 mg).

$^1$H-NMR (CDCl$_3$) δ ppm: 1.26 (3H, t, J=7.1 Hz), 1.59 (6H, s), 3.20 (2H, t, J=7.7 Hz), 3.54 (2H, t, J=7.7 Hz), 4.24 (2H, q, J=7.1 Hz), 6.69 (1H, dd, J=8.4, 2.6 Hz), 6.89 (1H, d, J=2.6 Hz), 7.11 (1H, d, J=8.4 Hz)

REFERENCE EXAMPLE 4

The following compounds were prepared according to a similar manner to that described in Reference Example 3 using the corresponding phenacyl bromide derivative.

Ethyl 2-[4-(2-bromoethyl)-2-chlorophenoxy]-2-methylpropionate $^1$H-NMR(CDCl$_3$) δ ppm: 1.27 (3H, t, J=7.1 Hz), 1.61 (6H, s), 3.07 (2H, t, J=7.6 Hz), 3.51 (2H, t, J=7.6 Hz), 4.25 (2H, q, J=7.1 Hz) 6.84 (1H, d, J=8.4 Hz), 6.96 (1H, dd, J=8.4, 2.2 Hz), 7.22 (1H, d, J=2.2 Hz)

Ethyl 2-[4-(2-bromoethyl)-2-methylphenoxy]-2-methylpropionate $^1$H-NMR(CDCl$_3$) δ ppm: 1.25 (3H, t, J=7.1 Hz), 1.58 (6H, s), 2.22 (3H, s), 3.05 (2H, t, J=7.8 Hz), 3.50 (2H, t, J=7.8 Hz), 4.24 (2H, q, J=7.1 Hz), 6.60 (1H, d, J=8.2 Hz), 6.87 (1H; dd, J=8.2, 1.9 Hz) 6.98 (1H, d, J=1.9 Hz)

REFERENCE EXAMPLE 5

Ethyl 2-[4-(2-hydroxyethyl)phenoxy]-2-methylpropionate

To a stirred solution of 2-(4-hydroxyphenyl)ethanol (1.4 g) in tetrahydrofuran (30 ml) was added 60% sodium hydride in mineral oil (405 mg) under ice-cooling, and the mixture was stirred for 1 hour at room temperature. To the stirred reaction mixture was added chloromethyl methyl ether (770 μl) under ice-cooling, and the resulting mixture was stirred for 16 hours at room temperature. Additionally, to the stirred reaction mixture was added 60% sodium hydride in mineral oil (405 mg) under ice-cooling. After the mixture was stirred for 1 hour at room temperature, benzyl bromide (1.2 ml) was added under ice-cooling and the resulting mixture was stirred for 16 hours at room temperature. The reaction mixture was poured into ice-water and extracted with diethyl ether. The extract was washed with brine and dried over anhydrous magnesium sulfate, and the solvent was removed under reduced pressure. The residue was dissolved in dichloromethane (20 ml), trifluoroacetic acid (20 ml) was added to the solution under ice-cooling with stirring, and the mixture was stirred for 1 hour. After the reaction mixture was concentrated under reduced pressure, 2N aqueous sodium hydroxide solution (20 ml) and water (20 ml) were added to the residue, and the resulting mixture was vigorously shaken. The aqueous layer was separated, washed with diethyl ether, acidified with concentrated hydrochloric acid and extracted with ethyl acetate. The extract was washed with a saturated aqueous sodium bicarbonate solution and brine, and dried over anhydrous magnesium sulfate, and the solvent was removed under reduced pressure. Purification of the residue by medium pressure liquid column chromatography on silica gel (eluent: hexane/diethyl ether=2/1) gave 4-(2-benzyloxyethyl)phenol (440 mg).

$^1$H-NMR (CDCl$_3$) δ ppm: 2.86 (2H, t, J=7.2 Hz), 3.65 (2H, t, J=7.2 Hz) 4.53 (2H, s), 4.79 (1H, s), 6.74 (2H, d, J=8.6 Hz), 7.08 (2H, d, J=8.6 Hz), 7.20–7.40 (5H, m)

To a stirred solution of 4-(2-benzyloxyethyl)phenol (420 mg) and 1,1,1-trichloro-2-methyl-2-propanol hydrate (690 mg) in acetone (5 ml) was added potassium hydroxide (320 mg) three times (total 960 mg) at intervals of 10 minutes under ice-cooling, and the mixture was stirred for 16 hours at room temperature. After the reaction mixture was concentrated under reduced pressure, the residue was dissolved in ice-water and washed with diethyl ether. The aqueous layer was acidified with concentrated hydrochloric acid and extracted with ethyl acetate. The extract was washed with brine and dried over anhydrous magnesium sulfate, and the solvent was removed under reduced pressure. A solution of thionyl chloride (400 μl) in ethanol (10 ml) was added to the residue, and the mixture was heated under reflux for 6 hours. After the reaction mixture was concentrated under reduced pressure, purification of the residue by medium pressure liquid column chromatography on silica gel (eluent: hexane/diethyl ether=5/1) gave ethyl 2-[4-(2-benzyloxy-ethyl)phenoxy]-2-methylpropionate (485 mg).

$^1$H-NMR (CDCl$_3$) δ ppm: 1.25 (3H, t, J=7.1 Hz), 1.57 (6H, s), 2.86 (2H, t, J=7.2 Hz), 3.65 (2H, t, J=7.2 Hz), 4.23 (2H, q, J=7.1 Hz) 4.52 (2H, s), 6.77 (2H, d, J=8.6 Hz), 7.08 (2H, d, J=8.6 Hz), 7.20–7.40 (5H, m)

To a solution of ethyl 2-[4-(2-benzyloxyethyl)-phenoxy]-2-methylpropionate (480 mg) in ethanol (3.0ml) was added 10% palladium on activated carbon (30 mg), and the mixture was stirred for 48 hours at room temperature under a hydrogen atmosphere. The catalyst was filtered off, and the solvent of the filtrate was removed under reduced pressure. Purification of the residue by medium pressure liquid column chromatography on silica gel (eluent: hexane/diethyl ether=1/1) gave ethyl 2-[4-(2-hydroxyethyl)phenoxy]-2-methylpropionate (310 mg).

$^1$H-NMR (CDCl$_3$) δ ppm: 1.26 (3H, t, J=7.1 Hz), 1.58 (6H, s), 2.80 (2H, t, J=6.5 Hz), 3.82 (2H, t, J=6.5 Hz), 4.24 (2H, q, J=7.1 Hz) 6.80 (2H, d, J=8.7 Hz), 7.09 (2H, d, J=8.7 Hz)

REFERENCE EXAMPLE 6
4-[2-(Benzyloxymethoxy)ethyl]aniline

To a stirred solution of 2-(4-aminophenyl) ethanol (5.0 g) in dichloromethane (50 ml) were added N,N-diisopropylethylamine (20 ml) and trifluoroacetic anhydride (6.6 ml) under ice-cooling, and the mixture was stirred for 1 hour at room temperature. The reaction mixture was poured into ice-water and extracted with ethyl acetate. The extract was washed with brine and dried over anhydrous magnesium sulfate. Removal of the solvent under reduced pressure gave 4'-(2-hydroxyethyl)-2,2,2-trifluoroacetanilide (6.2 g).

To a stirred solution of 4'-(2-hydroxyethyl)-2,2,2-trifluoroacetanilide (5.9 g) in tetrahydrofuran (20 ml) and dichloromethane (20 ml) were added N,N-diisopropylethylamine (5.7 ml) and benzyl chloromethyl ether (3.9 ml) under ice-cooling, and the mixture was stirred for 24 hours at room temperature. The reaction mixture was poured into ice-water and extracted with ethyl acetate. The extract was washed with brine and dried over anhydrous magnesium sulfate. Removal of the solvent under reduced pressure gave 4'-[2-(benzyloxymethoxy)ethyl]-2,2,2-trifluoroacetanilide (9.7 g).

To a solution of 4'-[2-(benzyloxymethoxy)ethyl]-2,2,2-trifluoroacetanilide (9.7 g) in methanol (50 ml) were added water (30 ml) and potassium carbonate (3.3 g), and the mixture was stirred for 24 hours at room temperature. The reaction mixture was poured into ice-water and extracted with ethyl acetate. The extract was washed with brine and dried over anhydrous magnesium sulfate. Removal of the solvent under reduced pressure gave 4-[2-(benzyloxymethoxy)ethyl]aniline (6.2 g).

$^1$H-NMR (CDCl$_3$) δ ppm: 2.80 (2H, t, J=7.1 Hz), 3.56 (2H, br s), 3.75 (2H, t, J=7.1 Hz), 4.52 (2H, s), 4.75 (2H, s), 6.63 (2H, d, J=8.5 Hz), 7.02 (2H, d, J=8.5 Hz), 7.20–7.40 (5H, m)

REFERENCE EXAMPLE 7
3-Chloro-4-[2-(methoxymethoxy)ethyl]aniline

To a stirred solution of 2-(2-chloro-4-nitrophenyl)-ethanol (2.9 g) in dichloromethane (20 ml) were added N,N-diisopropyl-ethylamine (3.0 ml) and chloromethyl methyl ether (1.2 ml) under ice-cooling, and the mixture was stirred for 18 hours at room temperature. The reaction mixture was poured into ice-water and extracted with ethyl acetate. The extract was washed with brine and dried over anhydrous magnesium sulfate, and the solvent was removed under reduced pressure. The residue was dissolved in methanol (20 ml), 3% platinum sulfide on activated carbon (wet) (842 mg) was added, and the mixture was stirred for 10 hours under a hydrogen atmosphere. After the catalyst was removed by filtration, the solvent was removed under reduced pressure to give 3-chloro-4-[2-(methoxy-methoxy)ethyl]aniline (2.0 g).

$^1$H-NMR (CDCl$_3$) δ ppm: 2.92 (2H, t, J=7.1 Hz), 3.31 (3H, s), 3.71 (2H, t, J=7.1 Hz), 3.70–3.90 (2H, m), 4.61 (2H, s), 6.54 (1H, dd, J=8.2, 2.4 Hz), 6.72 (1H, d, J=2.4 Hz), 7.04 (1H, d, J=8.2 Hz)

REFERENCE EXAMPLE 8
Methyl 2-[[4-(2-hydroyethyl)phenyl]amino]-2-methylpropionate To a stirred solution of 4-[2-(benzyloxymethoxy)-ethyl]aniline (1.4 g) and 1,1,1-trichloro-2-methyl-2-propanol hydrate (2.0 g) in acetone (10 ml) was added potassium hydroxide (2.9 g) three times (total 8.7 g) at intervals of 10 minutes under ice-cooling, and the mixture was stirred for 21 hours at room temperature. After the reaction mixture was concentrated under reduced pressure, the residue was dissolved in ice-water and washed with diethyl ether. The aqueous layer was neutralized with 2N hydrochloric acid, and the solvent was removed under reduced pressure. The residue was dissolved in a mixed solvent of dichloromethane (10 ml) and methanol (5.0 ml), a solution of diazomethane in diethyl ether was added until the reaction solution was colored, and the mixture was stirred for 3 hours at room temperature. After the reaction mixture was concentrated under reduced pressure, purification of the residue by flash column chromatography on silica gel (eluent: hexane/ethyl acetate=1/1) gave methyl 2-[[4-[2-(benzyl-oxymethoxy)ethyl]phenyl]amino]-2-methylpropionate (888 mg).

$^1$H-NMR (CDCl$_3$) δ ppm: 1.53 (6H, s), 2.79 (2H, t, J=7.1 Hz), 3.68 (3H, s), 3.76 (2H, t, J=7.1 Hz), 3.97 (1H, br), 4.52 (2H, s), 4.74 (2H, s), 6.52 (2H, d, J=8.6 Hz), 7.02 (2H, d, J=8.6 Hz), 7.25–7.40 (5H, m)

To a solution of methyl 2-[[4-[2-(benzyloxymethoxy)-ethyl]phenyl]amino]-2-methylpropionate (838 mg) in methanol (10 ml) was added 10% palladium on activated carbon (180 mg), and the mixture was stirred for 6 hours at room temperature under a hydrogen atmosphere. After the catalyst was removed by filtration, the filtrate was concentrated under reduced pressure to give methyl 2-[[4-(2-hydroyethyl)phenyl]amino]-2-methylpropionate (536 mg).

$^1$H-NMR (CDCl$_3$) δ ppm: 1.55 (6H, s), 2.76 (2H, t, J=6.5 Hz), 3.71 (3H, s), 3.75–3.90 (2H, m), 4.00 (1H, br), 6.53 (2H, d, J=8.5 Hz) 7.01 (2H, d, J=8.5 Hz)

REFERENCE EXAMPLE 9
Ethyl 2-[[3-chloro-4-(2-hydroxyethyl)phenyl]amino]-2-methylpropionate Ethyl 2-[[3-chloro-4-(2-hydroxyethyl)phenyl]amino]-2-methylpropionate was prepared according to a similar manner to that described in Reference Example 8 using 3-chloro-4-[2-(methoxymethoxy)ethyl]aniline with the exception of esterification by the treatment with thionyl chloride in ethanol solution and removal of methoxymethyl group.

¹H-NMR (CDCl₃) δ ppm: 1.21 (3H, t, J=7.1 Hz), 1.54 (6H, s), 2.89 (2H, t, J=6.7 Hz), 3.81 (2H, t, J=6.7 Hz), 4.19 (2H, q, J=7.1 Hz), 6.43 (1H, dd, J=8.3, 2.5 Hz), 6.61 (1H, d, J=2.5 Hz), 7.01 (1H, d, J=8.3 Hz)

REFERENCE EXAMPLE 10

Ethyl 2-[4-(2-bromoethyl)phenoxy]-2-methylpropionate

To a stirred solution of ethyl 2-[4-(2-hydroxyethyl)-phenoxy]-2-methylpropionate (474 mg) and triphenylphosphine (591 mg) in dichloromethane (10 ml) was added carbon tetrabromide (748 mg) under ice-cooling, and the mixture was stirred for 40 minutes. Rough purification of the reaction mixture by flash column chromatography on silica gel (eluent: diethylether) and further purification of the fraction by medium pressure liquid column chromatography on silica gel (eluent: hexane/diethyl ether=10/1) gave ethyl 2-[4-(2-bromoethyl)phenoxy]-2-methylpropionate (500 mg). ¹H-NMR (CDCl₃) δ ppm: 1.25 (3H, t, J=7.1 Hz), 1.59 (6H, s), 3.09 (2H, t, J=7.8 Hz), 3.52 (2H, t, J=7.8 Hz), 4.23 (2H, q, J=7.1 Hz) 6.79 (2H, d, J=8.7 Hz), 7.07 (2H, d, J=8.7 Hz)

REFERENCE EXAMPLE 11

The following compounds were prepared according to a similar manner to that described in Reference Example 10 using the corresponding phenethyl alcohol derivative.

Methyl 2-[[4-(2-bromoethyl),phenyl]amino]-2-methylpropionate

¹H-NMR (CDCl₃) δ ppm: 1.55 (6H, s), 3.03 (2H, t, J=7.9 Hz), 3.49 (2H, t, J=7.9 Hz), 3.70 (3H, s), 4.03 (1H, br s), 6.51 (2H, d, J=8.5 Hz), 6.99 (2H, d, J=8.5 Hz)

Ethyl 2-[[4-(2-bromoethyl)-3-chlorophenyl]amino]-2-methyl-propionate

¹H-NMR (CDCl₃) δ ppm: 1.20 (3H, t, J=7.1 Hz), 1.55 (6H, s), 3.14 (2H, t, J=7.8 Hz), 3.51 (2H, t, J=7.8 Hz), 4.13 (1H, br s), 4.18 (2H, q, J=7.1 Hz), 6.42 (1H, dd, J=8.3, 2.5 Hz), 6.58 (1H, d, J=2.5 Hz), 7.00 (1H, d, J=8.3 Hz)

Example 1

Ethyl 2-[3-chloro-4-[2-[[(1S,2R)-2-hydroxy-2-(4-hydroxyphenyl)-1-methylethyl]amino]ethyl]phenoxy]-1-2-methyl-propionate (Compound 1)

(1R,2S)-2-Amino-1-(4-hydroxyphenyl)propan-1-ol (70 mg) and ethyl 2-[4-(2-bromoethyl)-3-chlorophenoxy]-2-methyl-propionate (147 mg) were dissolved in N,N-dimethylformamide (2 ml), N,N-diisopropylethylamine (118 μl) was added to the solution, and the mixture was stirred for 2.5 hours at 80° C. After the reaction mixture was cooled, water was added to the reaction mixture, and the resulting mixture was extracted with ethyl acetate. The extract was washed with water and dried over anhydrous magnesium sulfate, and the solvent was removed under reduced pressure. Purification of the residue by medium pressure liquid column chromatography on aminopropyl silica gel (eluent: ethyl acetate/ethanol=20/1) gave ethyl 2-[3-chloro-4-[2-[[(1S,2R)-2-hydroxy-2-(4-hydroxyphenyl)-1-methylethyl]amino]ethyl]phenoxy]-2-methylpropionate (98 mg).

¹H-NMR (CDCl₃) δ ppm: 0.89 (3H, d, J=6.4 Hz), 1.29 (3H, t, J=7.1 Hz) 1.58 (3H, s), 1.59 (3H, s), 2.75–3.05 (5H, m), 3.20 (1H, br) 4.27 (2H, q, J=7.1 Hz), 4.56 (1H, d, J=4.9 Hz), 6.64 (1H, dd, J=8.4, 2.6 Hz), 6.76 (2H, d, J=8.5 Hz), 6.86 (1H, d, J=2.6 Hz), 7.01 (1H, d, J=8.4 Hz), 7.12 (2H, d, J=8.5 Hz)

Example 2

The following compounds were prepared according to a similar manner to that described in Example 1 using the corresponding phenethyl bromide derivative.

Ethyl 2-[4-[2-[[(1S,2R)-2-hydroxy-2-(4-hydroxyphenyl)-1-methylethyl]amino]ethyl]phenoxy]-2-methylpropionate (Compound 2)

¹H-NMR (CDCl₃) δ ppm: 0.92 (3H, d, J=6.4 Hz), 1.29 (3H, t, J=7.1 Hz) 1.57 (3H, s), 1.58 (3H, s), 2.65–2.85 (4H, m), 2.90–3.00 (1H, m), 4.28 (2H, q, J=7.1 Hz), 4.51 (1H, d, J=5.3 Hz), 6.72 (4H, d, J=8.6 Hz), 6.97 (2H, d, J=8.6 Hz), 7.07 (2H, d, J=8.6 Hz)

Ethyl 2-[2-chloro-4-[2-[[(1S,2R)-2-hydroxy-2-(4-hydroxyphenyl)-1-methylethyl]amino]ethyl]phenoxy]-2-methyl-propionate (Compound 3)

¹H-NMR(CD₃OD) δ ppm: 1.07 (3H, d, J=6.4 Hz), 1.26 (3H, t, J=7.1 Hz) 1.56 (6H, s), 2.50–2.90 (5H, m), 4.23 (2H, q, J=7.1 Hz), 4.39 (1H, d, J=6.2 Hz), 6.72 (2H, d, J=8.5 Hz), 6.80 (1H, d, J=8.4 Hz), 6.85–6.90 (1H, m), 7.09 (2H, d, J=8.5 Hz), 7.17 (1H, d, J=2.2 Hz)

Ethyl 2-[4-[2-[[(1S,2R)-2-hydroxy-2-(4-hydroxyphenyl)-1-methylethyl]amino]ethyl]-2-methylphenoxyl-2-methyl-propionate (Compound 4)

¹H-NMR(CD₃OD) δ ppm: 1.08 (3H, d, J=6.4 Hz), 1.23 (3H, t, J=7.1 Hz) 1.54 (6H, s), 2.14 (3H, s), 2.45–2.90 (5H, m), 4.21 (2H, q, J=7.1 Hz), 4.36 (1H, d, J-6.4 Hz), 6.53 (1H, d, J=8.3 Hz), 6.71 (2H, d, J=8.5 Hz), 6.75 (1H, dd, J=8.3, 2.0Hz), 6.84 (1H, d, J=2.0 Hz), 7.06 (2H, d, J=8.5 Hz)

Methyl 2-[[4-[2-[[(1S,2R)-2-hydroxy-2-(4-hydroxyphenyl)-1-methylethyl]amino]ethyl]phenyl]amino]-2-methylpropionate (Compound 5)

¹H-NMR (CDCl₃) δ ppm: 0.96 (3H, d, J=6.4 Hz), 1.55 (6H, s), 2.55–2.80 (4H, m), 2.90–3.00 (1H, m), 3.77 (3H, s), 4.48 (1H, d, J=5.6 Hz), 6.44 (2H, d, J=8.5 Hz), 6.71 (2H, d, J=8.5 Hz), 6.87 (2H, d, J=8.5 Hz), 7.05 (2H, d, J=8.5 Hz)

Ethyl 2-[3-chloro-4-[2-[[(1S,2 g)-2-hydroxy-2-(4-hydroxyphenyl)-1-methylethyl]amino]ethyl]phenyl]amino]-2-methyl-propionate (Compound 6)

¹H-NMR (CDCl₃) δ ppm: 0.93 (3H, d, J=6.4 Hz), 1.25 (3H, t, J=7.1 Hz) 1.54 (3H, s), 1.55 (3H, s), 2.70–2.90 (5H, m), 4.23 (2H, q, J=7.1 Hz), 4.54 (1H, d, J=5.2 Hz), 6.35 (1H, dd, J=8.3, 2.5 Hz) 6.54 (1H, d, J=2.5 Hz), 6.74 (2H, d, J=8.5 Hz), 6.87 (1H, d, J=8.3 Hz), 7.10 (2H, d, J=8.5 Hz)

Example 3

Ethyl 2-[3-chloro-4-[2-[[(1S,2R)-2-hydroxy-2-(4-hydroxyphenyl)-1-methylethyl]amino]ethyl]phenoxy]-2-methyl-propionate hydrochloride (Compound 7)

To a stirred solution of ethyl 2-[3-chloro-4-[2-[[(1S,2R)-2-hydroxy-2-(4-hydroxyphenyl)-1-methylethyl]-amino]ethyl]phenoxy]-2-methylpropionate (170 mg) in ethyl acetate (7.8 ml) was added 4N hydrogen chloride in ethyl acetate solution (200 μl) at room temperature. After the solvent was removed under reduced pressure, diethyl ether was added to the residue, and collection of the insoluble material by filtration gave ethyl 2-[3-chloro-4-[2-[[(1S,2R)-2-hydroxy-2-(4-hydroxyphenyl)-1-methylethyl]amino]ethyl]-phenoxy]-2-methyl-propionate hydrochloride (175 mg).

¹H-NMR(DMSO-d₆) δ ppm: 0.97 (3H, d, J=6.7 Hz), 1.18 (3H, t, J=7.1 Hz), 1.53 (6H, s), 3.05–3.40 (5H, m), 4.18 (2H, q, J=7.1 Hz) 5.08 (1H, br s), 5.90–6.00 (1H, m), 6.76 (2H, d, J=8.5 Hz), 6.79 (1H, dd, J=8.6, 2.6 Hz), 6.90 (1H, d, J=2.6 Hz), 7.17 (2H, d, J=8.5 Hz), 7.32 (1H, d, J=8.6 Hz), 8.94 (2H, br), 9.41 (1H, s)

Specific Rotation: $[\alpha]_D^{30}$=−8.4° (c=1.20, Ethanol)

Example 4

Ethyl 2-[4-[2-[[(1S,2R)-2-hydroxy-2-(4-hydroxyphenyl)-1-methylethyl]amino]ethyl]phenoxy]-2-methylpropionate hydrochloride (Compound 8)

Ethyl 2-[4-[2-[[(1S,2R)-2-hydroxy-2-(4-hydroxy-phenyl)-1-methylethyl]amino]ethyl]phenoxy]-2-methyl-propionate hydrochloride was prepared according to a similar manner to that described in Example 3 using ethyl 2-[4-[2-[[(1S,2R)-2-hydroxy-2-(4-hydroxyphenyl)-1-methylethyl]-amino]ethyl]phenoxy]-2-methylpropionate.

$^{1}$H-NMR(DMSO-d$_{6}$) δ ppm: 0.95 (3H, d, J=6.7 Hz), 1.18 (3H, t, J=7.1 Hz), 1.51 (6H, s), 2.90–3.00 (2H, m), 3.10–3.40 (3H, m) 4.16 (2H, q, J=7.1 Hz), 5.06 (1H, br s), 5.90–6.00 (1H, m), 6.70–6.80 (4H, m), 7.10–7.25 (4H, m), 8.80 (2H, br), 9.42 (1H, s)

Specific Rotation: $[\alpha]_D^{31}$=−11.3° (c=1.00, Ethanol)

Example 5

2-[3-Chloro-4-[2-[[(1S,2R)-2-hydroxy-2-(4-hydroxyphenyl)-1-methylethyl]amino]ethyl]phenoxy]-2-methylpropionic acid (Compound 9)

To a solution of ethyl 2-[3-Chloro-4-[2-[[(1S,2R)-2-hydroxy-2-(4-hydroxyphenyl)-1-methylethyl]amino]ethyl]-phenoxy]-2-methylpropionate (2.39 g) in ethanol (20 ml) was added 2N aqueous sodium hydroxide solution (8.2 ml), and the mixture was stirred for 13 hours at room temperature. To the stirred reaction mixture was added 2N hydrochloric acid (8.2 ml) under ice-cooling. After the reaction mixture was concentrated under reduced pressure, azeotropic concentration with ethanol was undergone. The residue was washed with water (180 ml) and dried under reduced pressure to give 2-[3-chloro-4-[2-[[(1S,2R)-2-hydroxy-2-(4-hydroxyphenyl)-1-methylethyl]amino]ethyl]phenoxy]-2-methylpropionic acid (2.02 g).

$^{1}$H-NMR (DMSO-d$_{6}$) δ ppm: 0.92 (3H, d, J=6.5 Hz), 1.48 (3H, s), 1.49 (3H, s), 2.70–3.10 (4H, m), 3.20–3.40 (1H, m), 5.05 (1H, br s), 6.65–6.80 (3H, m), 6.85 (1H, d, J=2.4 Hz), 6.95 (1H, d, J=8.5 Hz), 7.16 (2H, d, J=8.5 Hz)

Specific Rotation: $[\alpha]_D^{30}$=−5.3° (c=0.15, Methanol)

Example 6

The following compounds were prepared according to a similar manner to that described in Example 5 using the corresponding 2-methylpropionate derivative.

2-[4-[2-[[(1S,2R)-2-Hydroxy-2-(4-hydroxyphenyl)-1-methyl-ethyl]amino]ethyl]phenoxy]-2-methylpropionic acid (Compound 10)

$^{1}$H-NMR (DMSO-d$_{6}$) δ ppm: 0.91 (3H, d, J=6.6 Hz), 1.46 (6H, s), 2.60–2.80 (2H, m), 2.90–3.05 (2H, m), 3.15–3.35 (1H, m), 5.05 (1H, br s), 6.70–6.75 (4H, m), 6.86 (2H, d, J=8.6 Hz), 7.14 (2H, d, J=8.6 Hz), 9.40(1H, br)

Specific Rotation: $[\alpha]_D^{31}$=−13.1° (c=1.00, 1N Hydrochloric acid)

2-[2-Chloro-4-[2-[[(1S,2R)-2-hydroxy-2-(4-hydroxyphenyl)-1-methylethyl]amino]ethyl]phenoxy]-2-methylpropionic acid (Compound 11)

$^{1}$H-NMR(DMSO-d$_{6}$) δ ppm: 0.91 (3H, d, J=6.6 Hz), 1.50 (6H, s), 2.60–2.85 (2H, m), 2.90–3.50 (3H, m), 5.09 (1H, br s), 6.67 (1H, d, J=8.66 Hz), 6.72 (2H, d, J=8.55 Hz), 6.88 (1H, d, J=8.66 Hz), 7.15 (2H, d, J=8.5 Hz), 7.23 (1H, s), 9.35 (2H, br)

Specific Rotation: $[\alpha]_D^{31}$=−6.9° (c=0.75, Acetic acid)

2-[4-[2-[[(1S,2R)-2-Hydroxy-2-(4-hydroxyphenyl)-1-methyl-ethyl]amino]ethyl]-2-methylphenoxyl-2-methylpropionic acid (Compound 12)

$^{1}$H-NMR(DMSO-d$_{6}$) δ ppm: 0.92 (3H, d, J=6.6 Hz), 1.47 (6H, s), 2.11 (3H, s), 2.60–2.80 (2H, m), 2.85–3.05 (2H, m), 3.10–3.35(1H, m), 5.02 (1H, br s), 6.50–6.60 (1H, m), 6.65–6.75 (3H, m), 6.90 (1H, s), 7.13 (2H, d, J=8.5 Hz)

Specific Rotation: $[\alpha]_D^{31}$=−10.0° (c=0.36, Acetic acid)

2-[[4-[2-[[(1S,2R)-2-Hydroxy-2-(4-hydroxyphenyl)-1-methyl-ethyl]amino]ethyl]phenyl]amino]-2-methylpropionic acid (Compound 13)

$^{1}$H-NMR (DMSO-d$_{6}$+D$_{2}$O) δ ppm: 0.91 (3H, d, J=6.6 Hz), 1.37 (6H, s), 2.55–2.75 (2H, m), 2.85–3.00 (2H, m), 3.10–3.20 (1H, m), 4.92 (1H, d, J=2.2 Hz), 6.47 (2H, d, J=8.5 Hz), 6.70–6.80 (4H, m), 7.13 (2H, d, J=8.5 Hz)

Specific Rotation: $[\alpha]_D^{29}$=−8.2° (c=1.00, Acetic acid)

2-[[3-Chloro-4-[2-[[(1S,2R)-2-hydroxy-2-(4-hydroxyphenyl)-1-methylethyl]amino]ethyl]phenyl]amino]-2-methylpropionic acid (Compound 14)

$^{1}$H-NMR (DMSO-d$_{6}$) δ ppm: 0.88 (3H, d, J=6.6 Hz), 1.37 (6H, s), 2.60–2.90 (4H, m), 3.00–3.10 (1H, m), 4.83 (1H, br s), 6.40 (1H, dd, J=8.3, 2.4 Hz), 6.54 (1H, d, J=2.4 Hz), 6.71 (2H, d, J=8.6 Hz) 6.76 (1H, d, J=8.3 Hz), 7.11 (2H, d, J=8.6 Hz)

Test Example 1

The Experiment for Measuring β$_{3}$-Adrenoceptor Stimulating Effects

Urinary bladders of male ferrets (1100 to 1400 g in body weight) were isolated and urinary bladder smooth muscle strips of approximately 10 mm in length and approximately 2 mm in width were prepared. The experiment was conducted according to the Magnus method. The preparations with a tension of 1 g were exposed to Krebs-Henseleit solution maintained at 37° C. and gassed with a mixture of 95% oxygen and 5% carbon dioxide. Basal tensions of urinary bladder were isometrically measured with a force-displacement transducer and recorded on a rectigram. The drug was cumulatively added to the Magnus bath every about 5 minutes. The drug efficacy was evaluated as the concentration of the drug required to produce 50% of the relaxation before the addition of the drug (i.e., EC$_{50}$ value). In this experiment, tension of urinary bladder smooth muscle before the addition of the drug was expressed as 100% and tension of maximal relaxation after the addition of $10^{-5}$M concentration of forskolin was expressed as 0%. The result was shown in the following Table 1.

TABLE 1

| Compound No. | EC$_{50}$ (M) |
| --- | --- |
| 7 | $2.1 \times 10^{-8}$ |
| 9 | $1.9 \times 10^{-8}$ |
| 10 | $9.1 \times 10^{-9}$ |
| 11 | $2.4 \times 10^{-9}$ |
| 12 | $1.4 \times 10^{-8}$ |
| 13 | $2.3 \times 10^{-8}$ |
| 14 | $5.6 \times 10^{-9}$ |
| BRL-37344 | $1.6 \times 10^{-9}$ |

Test Example 2

The Experiment for Measuring β$_{1}$-Adrenoceptor Stimulating Effects

Atria of male SD rats (250 to 400 g in body weight) were isolated and the experiment was conducted according to the Magnus method. The preparations with a tension of 0.5 g were exposed to Krebs-Henseleit solution maintained at 37° C. and gassed with a mixture of 95% oxygen and 5% carbon dioxide. The cardiac contractility was isometrically measured with a force-displacement transducer, and heart rate was recorded on a rectigram via a tachometer. The drug was added cumulatively. The drug efficacy was evaluated as the concentration of the drug required to produce 50% increase of heart rate per minute (i.e., EC$_{50}$ value). In this experiment, increase of heart rate per minute after addition of $10^{-8}$M of isoproterenol was expressed as 100%. The result was shown in the following Table 2.

TABLE 2

| Compound No. | EC$_{50}$ (M) |
| --- | --- |
| 7 | 3.0 × 10$^{-7}$ |
| 9 | 3.5 × 10$^{-5}$ |
| 10 | 1.0 × 10$^{-4}$ |
| 11 | >10$^{-4}$ |
| 12 | >10$^{-4}$ |
| 13 | 3.9 × 10$^{-5}$ |
| 14 | 2.2 × 10$^{-6}$ |
| BRL-37344 | 2.7 × 10$^{-7}$ |

Test Example 3

The Experiment for Measuring $\beta_2$-Adrenoceptor Stimulating Effects

Uteri of pregnant SD rats (pregnancy day 21) were isolated and longitudinal strips of approximately 15 mm in length and approximately 5 mm in width free from the basal plate were prepared. The experiment was conducted according to the Magnus method. The preparations with a tension of 0.5 g were exposed to Locke-Ringer solution maintained at 37° C. and gassed with a mixture of 95% oxygen and 5% carbon dioxide. Spontaneous contractions of myometrium were isometrically measured with a force-displacement transducer and recorded on a rectigram. The drug was cumulatively added to the Magnus bath every 5 minutes. The drug efficacy was evaluated as the concentration of the drug required to produce 50% of the inhibition of uterine contraction (i.e., EC$_{50}$ value) by comparing the sum of uterine contraction during 5 minutes after the addition of the drug with the sum of uterine contractions during 5 minutes before the addition of the drug which was expressed as 100%. The result was shown in the following Table 3.

TABLE 3

| Compound No. | EC$_{50}$ (M) |
| --- | --- |
| 7 | 4.5 × 10$^{-8}$ |
| 9 | 3.1 × 10$^{-6}$ |
| 10 | 3.9 × 10$^{-6}$ |
| 11 | 3.8 × 10$^{-5}$ |
| 12 | >10$^{-4}$ |
| 13 | 1.1 × 10$^{-5}$ |
| 14 | 1.4 × 10$^{-6}$ |
| BRL-37344 | 9.0 × 10$^{-9}$ |

Test Example 4

Acute Toxicity Test

To male ICR rats of 4 weeks age was administered intravenously 2-[3-chloro-4-(2-[[(1S,2R)-2-hydroxy-2-(4-hydroxyphenyl)-1-methylethyl]amino]ethyl]phenoxy]-2-methyl-propionic acid at a dose of 400 mg/kg. No death of animals was observed during 24 hours after the administration with the time course.

Industrial Applicability

The 2-methylpropionic acid derivatives represented by the above general formula (I) and pharmaceutically acceptable salts thereof of the present invention have excellent $\beta_3$-adronoceptor stimulating effects and are useful as agents for the prevention or treatment of obesity, hyperglycemia, the diseases caused by intestinal hypermotility, pollakiuria, urinary incontinence, depression, the diseases caused by biliary calculi or hypermotility of biliary tract, or the like.

What is claimed is:

1. A 2-methyipropionic acid derivative represented by the general formula:

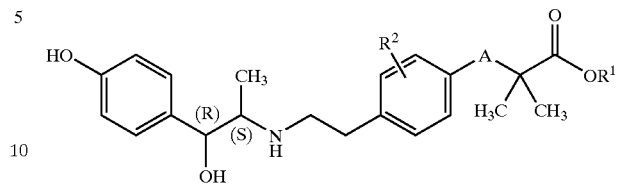

wherein R$^1$ represents a hydrogen atom, a lower alkyl or an aralkyl group; R$^2$ represents a hydrogen atom, a lower alkyl group or a halogen atom; A represents an oxygen atom; the carbon atom marked with (R) represents a carbon atom in R configuration; and the carbon atom marked with (S) represents a carbon atom in S configuration or a pharmaceutically acceptable salt thereof.

2. A 2-methylpropionic acid derivative as claimed in claim 1, represented by the general formula:

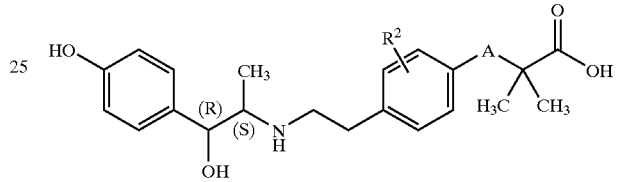

wherein R$^2$ represents a hydrogen atom, a lower alkyl group or a halogen atom; A represents an oxygen atom; the carbon atom marked with (R) represents a carbon atom in R configuration; and the carbon atom marked with (S) represents a carbon atom in S configuration or a pharmaceutically acceptable salt thereof.

3. A pharmaceutical composition comprising as the active ingredient a 2-methylpropionic acid derivative as claimed in claim 1, or a pharmaceutically acceptable salt thereof with a pharmaceutically acceptable carrier or excipient.

4. A composition for the treatment of obesity, hyperglycemia, the diseases caused by intestinal hypermotility, pollakiuria, urinary incontinence, depression, or the diseases caused by biliary calculi or hypermotility of biliary tract which comprises as the active ingredient a 2-methylpropionic acid derivative as claimed in claim 1, or a pharmaceutically acceptable salt thereof, with a pharmaceutically acceptable carrier or excipient.

5. A method for the treatment of obesity, hyperglycemia, the diseases caused by intestinal hypermotility, pollakiuria, urinary incontinence, depression, or the diseases caused by biliary calculi or hypermotility of biliary tract which comprises administering a therapeutically effective amount of a 2-methylpropionic acid derivative as claimed in claim 1, or a pharmaceutically acceptable salt thereof.

6. A pharmaceutical composition as the active ingredient a 2-methyipropionic acid derivative as claimed in claim 2, or a pharmaceutically acceptable salt thereof, with a pharmaceutically acceptable carrier or excipient.

7. A composition for the treatment of obesity, hyperglycemia, the diseases caused by intestinal hypermotility, pollakiuria, urinary incontinence, depression or the diseases caused by biliary calculi or hypermotility of biliary tract which comprises as the active ingredient a 2-methylpropionic acid derivative as claimed in claim 2, or a pharmaceutically acceptable salt thereof, with a pharmaceutically acceptable carrier or excipient.

8. A method for the treatment of obesity, hyperglycemia, the diseases caused by intestinal hypermotility, pollakiuria, urinary incontinence, depression, or the diseases caused by biliary calculi or hypermotility of biliary tract which comprises administering a therapeutically effective amount of a 2-methylpropionic acid derivative as claimed in claim 2, or a pharmaceutically acceptable salt thereof.

9. A process for the manufacture of a pharmaceutical composition which comprises mixing a 2-methylpropionic acid derivative as claimed in claim 1, or a pharmaceutically acceptable salt thereof, with a pharmaceutically acceptable carrier or excipient.

10. A process for the manufacture of a pharmaceutical composition which comprises mixing a 2-methyipropionic acid derivative as claimed in claim 2, or a pharmaceutically acceptable salt thereof, with a pharmaceutically acceptable carrier or excipient.

* * * * *